United States Patent [19]

Nagata et al.

[11] Patent Number: 4,625,062

[45] Date of Patent: Nov. 25, 1986

[54] PROCESS FOR PRODUCING 4-ALKOXYANILINES

[75] Inventors: Teruyuki Nagata; Akihiro Tamaki; Hiroki Ohnishi; Hideki Mizuta, all of Ohmuta, Japan

[73] Assignee: Mitsui Toatsu Chemicals, Inc., Tokyo, Japan

[21] Appl. No.: 675,225

[22] Filed: Nov. 27, 1984

[30] Foreign Application Priority Data

Nov. 28, 1983 [JP] Japan .................................. 58-222237

[51] Int. Cl.$^4$ .............................................. C07C 85/11
[52] U.S. Cl. .................................... 564/416; 564/417; 564/418; 564/442; 564/443
[58] Field of Search ............... 564/416, 417, 418, 443, 564/442; 570/145

[56] References Cited

U.S. PATENT DOCUMENTS

3,383,416  5/1968  Benner ................................. 564/418
3,929,891 12/1975  Habig et al. ......................... 564/417

FOREIGN PATENT DOCUMENTS

520347  8/1976  U.S.S.R. ............................... 564/418

OTHER PUBLICATIONS

Journal of the Chemical Society of Japan, 1979, (11), pp. 1532 to 1535.
Journal of the Chemical Society of Japan, 1982, (7), pp. 1237 to 1240.
Journal of the Chemical Society of Japan, 1980, (2), pp. 245 to 249.

Primary Examiner—Charles F. Warren
Assistant Examiner—John A. Sopp
Attorney, Agent, or Firm—Fisher, Christen & Sabol

[57] ABSTRACT

4-Alkoxyanilines are obtained industrially advantageously by catalytically hydrogenating a nitrobenzene in the presence of a noble metal catalyst in a mixed solvent containing a lower aliphatic alcohol, sulfuric acid, and water or a lower aliphatic carboxylic acid or both to induce hydrogenation and a Bamberger-type rearrangement reaction. The mixed solvent contains at least 10 moles, preferably 30 to 60 moles, of the lower aliphatic alcohol per mole of the nitrobenzene, 1 to 10 moles, preferably 2 to 7 moles, of sulfuric acid per mole of the nitrobenzene, and 2 to 30% by weight, preferably 3 to 10% by weight, of water, the lower aliphatic carboxylic acid or both.

9 Claims, No Drawings

PROCESS FOR PRODUCING 4-ALKOXYANILINES

This invention relates to a process for producing 4-alkoxyanilines. More specifically, it relates to an industrially advantageous process for producing 4alkoxyanilines, which comprises catalytically hydrogenating a nitrobenzene represented by the general formula

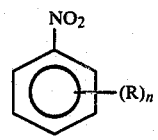

wherein R represents a hydrogen atom, a halogen atom, a lower alkyl group or a lower alkoxy group, and n is 1 or 2, provided that when R is other than hydrogen, it is bonded to the o-position and/or the m-position to the nitro group, in the presence of a noble metal catalyst in a mixed solvent containing a lower aliphatic alcohol, sulfuric acid, and water or a lower aliphatic carboxylic acid or 4-Alkoxyanilines are important intermediates of dyes and medicines. In particular, 2-methyl-4-methoxyaniline is useful as an intermediate of fluoranseries black dyes.

Previously, the 4-alkoxyanilines have been produced from nitrobenzenes through a number of steps, and the total yields of the products and the economy of the processes practiced have proved to be very unsatisfactory.

In recent years, attempts were made to produce 4-alkoxyanilines in one step from the nitrobenzenes of the above general formula (I) in the presence of noble catalysts in a substantially anhydrous mixed solvent composed of an alcohol and sulfuric acid. For example, Journal of the Chemical Society of Japan [1979 (11), page 1532] reported that 2,4-dimethoxyaniline was obtained in a maximum yield of 27.8% from o-nitroanisole as a material by adding dimethyl sulfoxide (DMSO for short) as a catalyst poison to the reaction system. Journal of the Chemical Society of Japan [1980 (2), page 245] states that 2.2% of p-anisidine was obtained from nitrobenzene, and particularly, when o-methylnitrobenzene was used as a starting material, 2-methyl-4-methoxyaniline was obtained in a maximum yield of 70.2% by adding DMSO (in the absence of DMSO, the yield was 48.3%). Journal of the Chemical Society of Japan [1982 (7), page 1237], subsequently published, reported that 2,3-dimethyl-p-anisidine, 2,6-dimethyl-p-anisidine, 1-amino-4-methoxy-naphthalene, and 1-amino-2-methyl-4-methoxy-naphthalene were obtained from the corresponding nitro compounds in the presence of DMSO in a maximum yield of 67.4% (63.7% in the absence of DMSO), 72.1% (45.2% in the absence of DMSO), 68%, and 55%, respectively. Furthermore, it was reported long ago that p-anisidine was obtained in a yield of about 40% from phenylhydroxylamine in a mixed solvent of methanol and sulfuric acid [Ber., 31, 1500 (1898)].

However, processes for producing 4-alkoxyanilines in one step by catalytically hydrogenating nitro compounds in the presence of noble metal catalyst utilizing the Bamberger-type rearrangement reaction as described in the above-cited papers in the Journal of the Chemical Society of Japan generally give low yields, and cannot be said to be industrially feasible. As an attempt to improve such processes, there were suggested processes as described above in which commercially acceptable yields are obtained by adding DMSO. Since, however, DMSO is a very strong catalyst poison, the expensive noble metal catalysts recovered cannot substantially be re-used. Hence, these processes are very uneconomical for industrial practice.

The present invention provides an industrially advantageous improved process for producing 4-alkoxyanilines from nitrobenzenes by catalytic hydrogenation. More specifically, this invention provides a process for producing 4-alkoxyanilines of high purity in high yields from nitrobenzenes, characterized in that the nitrobenzenes are catalytically hydrogenated in the presence of a noble metal catalyst in a mixed solvent obtained by adding a specified amount of water, a lower aliphatic carboxylic acid, or both instead of DMSO in the conventional processes to a mixture of a lower aliphatic alcohol and sulfuric acid.

It has been found surprisingly that according to the process of this invention, by performing the reaction in a mixed solvent prepared by adding a predetermined amount of water and/or a lower aliphatic carboxylic acid to a mixture of predetermined amounts of sulfuric acid and a lower aliphatic alcohol, the final desired product can be obtained in high yields despite the complete absence of DMSO, and that the expensive noble metal catalyst used in the reaction can be repeatedly used for the same reaction.

The reaction solvent used in the process of this invention is a mixed solvent obtained by adding 2 to 30% by weight, preferably 3 to 10% by weight, of water, a lower aliphatic carboxylic acid or both to a mixture of a lower aliphatic alcohol and sulfuric acid. If the content of water and/or the aliphatic carboxylic acid is outside the above-specified range, the production of 4-hydroxyanilines and/or anilines as by-products undesirably increases. The content of the lower aliphatic alcohol in the mixed solvent is at least 10 moles, preferably 20 to 100 moles, more preferably 30 to 60 moles, per mole of the starting nitrobenzenes. If it is less than 10 moles, the yield of the desired product is low. Excessively large amounts make the process uneconomical. The content of sulfuric acid in the mixed solvent is 1 to 10 moles, preferably 2 to 7 moles, per mole of the starting nitrobenzenes. If the content of sulfuric acid is outside this range, there is an appreciably increased formation of anilines and/or unknown tarry components. If the amount of sulfuric acid becomes excessively large, the reaction time becomes longer, and a marked increase in the formation of unknown tarry components is observed.

The amount of the mixed solvent used should be selected by considering the optimum concentration of the starting nitrobenzene charged and the optimum composition of the mixed solvent which ensure high yields of the final desired product and can avoid the complexity of withdrawal of the product after the reaction. Usually, the suitable concentration of the nitrobenzene charged is 5 to 20% by weight, the suitable concentration of the lower aliphatic alcohol in the mixed solvent is 70 to 90% by weight and the suitable concentration of sulfuric acid in the solvent is about 5 to 25% by weight.

In the mixed solvent, water and the lower aliphatic carboxylic acid may be present singly or in combination. Accordingly, the lower aliphatic carboxylic acid may be used as an aqueous solution. When it is used as an aqueous solution, considerations must be given so that at least 2% by weight of the lower aliphatic carboxyilc acid is present in the mixed solvent and water is present in a specified amount. Suitable lower aliphatic carboxylic acids are, for example, acetic acid, propionic acid, butyric acid and valerianic acid. Acetic acid an propionic acid are preferred among these carboxylic acids, and acetic acid is especially preferred.

In the process of this invention, the reaction temperature is selected within the range from 0° C. to the boiling point of the mixed solvent, preferably from 30° to 60° C.

Reaction presures from atmospheric pressure to 2 kg/cm$^2$-G are suitable for practical purposes. High pressures are unnecessary and rather tend to increase the amount of by-product anilines.

The noble catalyst that can be used in this invention includes, for example, platinum, palladium and a mixture of these. The metal catalyst is used on an inert solid carrier, and carbon is advantageous as the carrier. A catalyst containing 1-5% platinum and/or palladium on activated carbon is preferred. Catalysts containing 0.1 to 20% of such metals are feasible in the process of this invention. It is preferred to use a supported catalyst in a catalytic amount corresponding to 0.01 to 0.10% by weight platinum or palladium based on the nitrobenzene to be reacted.

Examples of the lower aliphatic alcohols are methanol, ethanol and propanol. Lower aliphatic alcohols having up to 3 carbon atoms are advantageous. Methanol is most preferred because it leads to the formation of the desired product in a particularly high yield.

The hydrogenation of the nitrobenzene is carried out under the foregoing conditions, and the desired product can be withdrawn in the following manner. First, the reaction mixture after the reaction is filtered to recover the catalyst (which is recycled to the next reaction). Then, the alcohol is evaporated. The residue, after adding water if required, is neutralized to a pH of 7 to 8. The neutralized solution is extracted with a suitable organic solvent such as ethyl acetate, benzene or monochlorobenzene. The oily layer is distilled under reduced pressure to give the 4-alkoxyaniline.

According to the process of this invention, the 4-alkoxyanilines can be produced in high yields. Since the process does not at all use a substance which becomes a catalyst poison in catalytic hydrogenation, such as DMSO, the expensive noble metal catalyst can be repeatedly used without any consequent decrease in yield. This is a great industrial advantage. Particularly, in the production of 2-methyl-4-methoxyaniline from o-nitrotoluene, a high yield can be maintained to great industrial advantage.

The following examples illustrate the present invention specifically.

EXAMPLE 1

A 5-liter glass reactor equipped with a stirrer, a thermometer and a hydrogen introducing tube was charged with 137.1 g (1.0 mole) of o-nitrotoluene, 264.5 g (2.6 moles) of 98% sulfuric acid, 68.6 g of distilled water, 1518.0 g (47.4 moles) of methanol and 0.41 g of 3% platinum on carbon as a hydrogenation catalyst.

The reaction was carried out at 50° C. under a slightly elevated pressure of 20 to 30 cmH$_2$O while adding hydrogen. The reaction required a period of 300 minutes with the absorption of 52.5 liters until its termination. At this time, the o-nitrotoluene scarcely remained in the reaction solution.

Subsequently, the reaction solution was filtered to separate the catalyst. Methanol was evaporated from the filtrate, and 500 g of distilled water was added. The mixture was neutralized to a pH of 7.2 with 28% aqueous ammonia. The neutralized solution was extracted with 200 g of toluene. The toluene layer was washed with a dilute aqeuous solution of sodium hydroxide, concentrated and distilled under reduced pressure. There were obtained 22.8 g of o-toluidine as an initial distillate and 96.8 g (yield 70.0%) of 2-methyl-4-methoxyaniline (boiling point 136°–138° C./20 mmHg) as a main distillate. The main distillate was found to have a purity of 99.2% by gas chromatography.

Elemental analysis of the main distillate for

| C$_8$H$_{11}$NO: | C | H | N |
|---|---|---|---|
| Calculated (%): | 70.0 | 8.08 | 10.2 |
| Found (%): | 69.8 | 7.98 | 10.3 |

EXAMPLE 2

The same reactor as used in Example 1 was charged with 137.1 g (1.0 mole) of o-nitrotoluene, 264.5 g (2.6 moles) of 98% sulfuric acid, 68.6 g of distilled water, 1518.0 g (47.4 moles) of methanol and 0.86 g (containing water) of the catalyst recovered from the process described in Example 1.

The reaction was carried out in the same way as in Example 1. The reaction required a period of 310 minutes with the absorption of 52.0 liters of water until its termination.

Subsequently, the reaction solution was worked up in the same way as in Example 1 to give 22.3 g of o-toluidine and 97.6 g (yield 70.6%) of 2-methyl-4-methoxyaniline. The 2-methyl-4-methoxyaniline was found to have a purity of 99.2% by gas chromatography.

EXAMPLE 3

The same catalytic reduction reaction as in Example 2 was repeated except that the catalyst recovered from the process of Example 2 was used instead of the catalyst recovered from the process of Example 1. The reaction required a period of 310 minutes, and 2-methyl-4-methoxyaniline was obtained in a yield of 70.4%.

EXAMPLE 4

The same catalytic reduction reaction as in Example 2 was repeated except that the catalyst recovered from the process of Example 3 was used instead of the catalyst recovered from the process of Example 1. The reaction required a period of 320 minutes, and 2-methyl-4-methoxyaniline was obtained in a yield of 70.7%.

EXAMPLE 5

The same catalytic reduction reaction as in Example 2 was repeated except that the catalyst recovered from the process of Example 4 was used instead of the catalyst recovered from the process of Example 1. The reaction required a period of 320 minutes, and 2-methyl-4-methoxyaniline was obtained in a yield of 71.0%.

EXAMPLE 6

The same catalytic reduction reaction as in Example 2 was repeated except that 0.13 g of the same fresh catalyst as used in Example 1 was added to the catalyst recovered from the process of Example 5. The reaction required a period of 290 minutes with the absorption of 53.5 liters of hydrogen until its termination. The reaction solution was worked up in the same way as in Example 1 to give 22.5 g of o-toluidine and 97.5 g (yield 70.7%) of 2-methyl-4-methoxyaniline. The 2-methyl-4-methoxyaniline was found to have a purity of 99.4% by gas chromatography.

EXAMPLE 7

The same catalytic reduction reaction as in Example 1 was repeated except that 68.6 g (0.5 mole) of o-nitrotoluene was used. The reaction required a period of 220 minutes with the absorption of 26.4 liters of hydrogen until its termination. The reaction solution was worked up in the same way as in Example 1 to give 9.6 g of o-toluidine and 52.1 g (yield 75.2%) of 2-methyl-4-methoxyaniline. The 2-methyl-4-methoxyaniline was found to have a purity of 99.0% by gas chromatography.

COMPARATIVE EXAMPLE 1

The same catalytic reduction reaction as in Example 1 was repeated except that distilled water was not used. The reaction required 1100 minutes with the absorption of 57.0 liters of hydrogen until its termination. The reaction solution was worked up in the same way as in Example 1. There were only obtained 24.3 g of o-toluidine and 72.5 g (yield 52.5%) of 2-methyl-4-methoxyaniline. The 2-methyl-4-methoxyaniline was found to have a purity of 99.3% by gas chromatography.

EXAMPLE 8

The same catalytic reduction reaction as in Example 1 was carried out except that o-nitrotoluene was used in an amount of 68.6 g (0.5 mole), and 68.6 g of glacial acetic acid was used instead of distilled water. The reaction required a period of 220 minutes with the absorption of 26.4 liters of hydrogen until its termination. The reaction solution was worked up in the same way as in Example 1 to give 9.0 g of o-toluidine and 53.1 g (yield 76.6%) of 2-methyl-4-methoxyaniline. The 2-methyl-4-methoxyaniline was found to have a purity of 99.0% by gas chromatography.

COMPARATIVE EXAMPLE 2

The same catalytic reduction reaction as in Example 8 was repeated except that glacial acetic acid was not fed. The reaction required a period of 1100 minutes with the absorption of 57.0 liters of hydrogen until its termination. The reaction solution was worked up in the same way as in Example 1. But there were obtained only 24.3 g of o-toluidine and 72.5 g (yield 52.5%) of 2-methyl-4-methoxyaniline. The 2-methyl-4-methoxyaniline was found to have a purity of 99.3% by gas chromatography.

EXAMPLE 9

The same catalytic reduction reaction as in Example 1 was carried out except that 157.6 g (1.0 mole) of o-chloronitrobenzene was used instead of 137.1 g (1.0 mole) of o-nitrotoluene. The reaction required a period of 480 minutes with the absorption of 53.0 liters of hydrogen until its termination. Subsequently, the reaction solution was worked up in the same way as in Example 1 to give 8.9 g of o-chloroaniline as an initial distillate and 102.9 g (yield 65.0%) of 2-chloro-4-methoxyaniline (boiling point 141°-143° C./20 mmHg) as a main distillate. The main distillate was found to have a purity of 99.5% by gas chromatography.

| Elemental analysis of the main distillate for $C_7H_8ClNO$: | | | |
|---|---|---|---|
| | C | H | N | Cl |
| Calculated (%): | 53.5 | 5.12 | 8.89 | 22.5 |
| Found (%): | 53.1 | 5.07 | 8.84 | 22.2 |

EXAMPLE 10

The same catalytic reduction reaction as in Example 1 was repeated except that 151.2 g (1.0 mole) of 2,6-dimethyl-nitrobenzene was used instead of 137.1 g (1.0 mole) of o-nitrobenzene. The reaction required a period of 290 minutes with the absorption of 53.8 liters of hydogen until its termination. Subsequently, the reaction solution was worked up in the same way as in Example 1 to give 25.0 g of 2,6-dimethylaniline as an initial distillate and 108.9 g (yield 71.8%) of 2,6-dimethyl-4-methoxyaniline as a main distillate. The main distillate was found to have a purity of 99.7% by gas chromatography.

EXAMPLE 11

The same catalytic reduction reaction as in Example 1 was carried out except that 157.6 g (1.0 mole) of o-chloronitrobenzene was used instead of 137.1 g (1.0 mole) of o-nitrotoluene and a 50% aqueous solution of acetic acid was used instead of distilled water. The reaction required a period of 480 minutes with the absorption of 53.0 liters of hydrogen until its termination. Subsequently, the reaction solution was worked up in the same way as in Example 1 to give 8.5 g of o-chloroaniline as an initial distillate and 103.7 g (yield 65.5%) of 2-chloro-4-methoxyaniline (boiling point 141° to 143° C./20 mmHg) as a main distillate. The main distillate was found to have a purity of 99.5% by gas chromatography.

| Elemental analysis of the main distillate for $C_7H_8ClNO$: | | | |
|---|---|---|---|
| | C | H | N | Cl |
| Calculated (%): | 53.3 | 5.12 | 8.89 | 22.5 |
| Found (%): | 53.2 | 5.09 | 8.84 | 22.2 |

EXAMPLE 12

The same catalytic reduction reaction as in Example 1 was repeated except that propionic acid was used instead of distilled water. The reaction ended in 320 minutes. The reaction solution was worked up in the same way as in Example 1 to give 22.0 of o-toluidine and 98.3 g (yield 71.1%) of 2-methyl-4-methoxyaniline.

EXAMPLE 13

The same catalytic reduction reaction as in Example 1 wa repeated except that the amount of distilled water was changed to 264.5 g. The reaction ended in 270 minutes. The reaction solution was worked up in the same way as in Example 1 to give 23.1 g of o-toluidine and 83.6 g (yield 60.5%) of 2-methyl-4-methoxyaniline. 17.6 g of 2-methyl-4-hydroxyaniline was also formed as a by-product.

EXAMPLE 14

The same catalytic reduction reaction as in Example 1 was repeated except that the amount of 98% sulfuric acid was changed to 1000 g, or in other words, a mixed solvent composed of 58.7% by weight of methanol, 37.9% by weight of sulfuric acid and 3.4% by weight of water was used. The reaction required a period of 1050 minutes until its termination. The reaction solution was worked up in the same weay as in Example 1 to give 20.5 g of o-toluidine and 89.9% (yield 65.0%) of 2-methyl-4-methoxyaniline.

What is claimed is:

1. Process for producing a 4-alkoxyaniline, which comprises catalytically hydrogenating a nitrobenzene represented by the following formula:

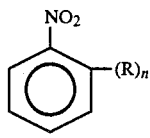 (I)

wherein R represents a hydrogen atom, a halogen atom, a lower alkyl group or a lower alkoxy group, and n is 1 or 2, provided that when R is other than hydrogen, it is bonded to the o-position and/or the m-position to the nitro group, in the presence of a catalytically effective amount of a noble metal catalyst which is selected from the group consisting of (i) platinum on activated carbon, (ii) palladium on activated carbon and (iii) mixture of platinum and palladium on activated carbon, in a mixed solvent containing a lower aliphatic alcohol, sulfuric acid, and water or a lower aliphatic carboxylic acid or both, said mixed solvent comprising at least 10 moles, per mole of the nitrobenzene, of the lower aliphatic alcohol, 1 to 10 moles, per mole of the nitrobenzene, of sulfuric acid, and 2 to 30 percent by weight of water, the lower aliphatic carboxylic acid or both, at a temperature of from 0° C. to the boiling point of the mixed solvent and at a pressure of from atmospheric pressure to 2 kg/cm$^2$-G.

2. The process of claim 1 wherein 1 to 5 weight percent of platinum, palladium or a mixture thereof is on the inert solid carrier.

3. The process of claim 1 wherein 0.01 to 0.10 weight percent of platinum or palladium is used based on the amount of nitrobenzene to be reacted.

4. The process of claim 1 wherein the content of water, the lower aliphatic alcohol or both in the mixed solvent is 3 to 10 percent by weight.

5. The process of claim 1 wherein the content of the lower aliphatic alcohol in the mixed solvent is 30 to 60 moles per mole of the nitrobenzene.

6. The process of claim 1 wherein the content of sulfuric acid in the mixed solvent is 2 to 7 moles per mole of the nitrobenzene.

7. The process of claim 1 wherein the lower aliphatic alcohol is methanol.

8. The process of claim 1 wherein the lower aliphatic carboxylic acid is acetic acid.

9. The process of claim 1 wherein the nitrobenzene is o-nitrotoluene.

* * * * *